(12) United States Patent
Yang

(10) Patent No.: US 8,075,525 B2
(45) Date of Patent: Dec. 13, 2011

(54) SHEET FOR GUIDING LOCATION OF INSULIN INJECTION

(75) Inventor: Sung-Bo Yang, Seoul (KR)

(73) Assignee: Lilly Korea, Ltd., Seoul (KR)

( * ) Notice: Subject to any disclaimer, the term of this patent is extended or adjusted under 35 U.S.C. 154(b) by 0 days.

(21) Appl. No.: 12/697,333

(22) Filed: Feb. 1, 2010

(65) Prior Publication Data

US 2010/0198153 A1     Aug. 5, 2010

(30) Foreign Application Priority Data

Feb. 2, 2009    (KR) .................... 20-2009-0001053 U

(51) Int. Cl.
*A61M 5/42*      (2006.01)
(52) U.S. Cl. .................. 604/116; 604/181; 604/189
(58) Field of Classification Search ............... 604/181, 604/186, 189, 116; 206/459.1, 459.5, 534; 116/317–318, 319, 323; 221/1–2, 4–5
See application file for complete search history.

(56) References Cited

U.S. PATENT DOCUMENTS

| | | | |
|---|---|---|---|
| 3,542,022 A * | 11/1970 | Bartnik .................. | 604/116 |
| 3,999,504 A | 12/1976 | Kearse | |
| 4,228,796 A * | 10/1980 | Gardiner ................. | 604/116 |
| 4,500,021 A * | 2/1985 | Bildusas .................. | 225/49 |
| 6,319,467 B1 * | 11/2001 | McLernon, III .......... | 600/556 |
| 2004/0031719 A1* | 2/2004 | Weinstein ................ | 206/534 |
| 2008/0020151 A1* | 1/2008 | Li ........................ | 428/32.34 |

FOREIGN PATENT DOCUMENTS

| | | |
|---|---|---|
| KR | 20-0213301 Y1 | 11/2000 |
| KR | 20-0400384 Y1 | 11/2005 |

OTHER PUBLICATIONS

International Search Report, Appln No. PCT/KR2010/000546, dated Nov. 1, 2010.

* cited by examiner

*Primary Examiner* — Nicholas D Lucchesi
*Assistant Examiner* — Quynh-Nhu H Vu
(74) *Attorney, Agent, or Firm* — Kile Park Goekjian Reed & McManus PLLC

(57) ABSTRACT

A sheet for guiding location of insulin injection has a sheet shape. The sheet has a first face and a second face opposite to the first face. A reference mark is formed at a first portion of the sheet to correspond to user's navel. A plurality of injection holes is formed at a second portion of the sheet opposite to the first portion to inject insulin, so that the insulin is injected at a left portion with respect to the reference mark by using the first face and the insulin is injected at a right portion with respect to the reference mark. A manual of the sheet is indicated on the first face and/or the second face. A day of a week is indicated corresponding to and adjacent to each of the injection holes. Thus, patient's convenience may be enhanced.

8 Claims, 3 Drawing Sheets

[FIG. 1]
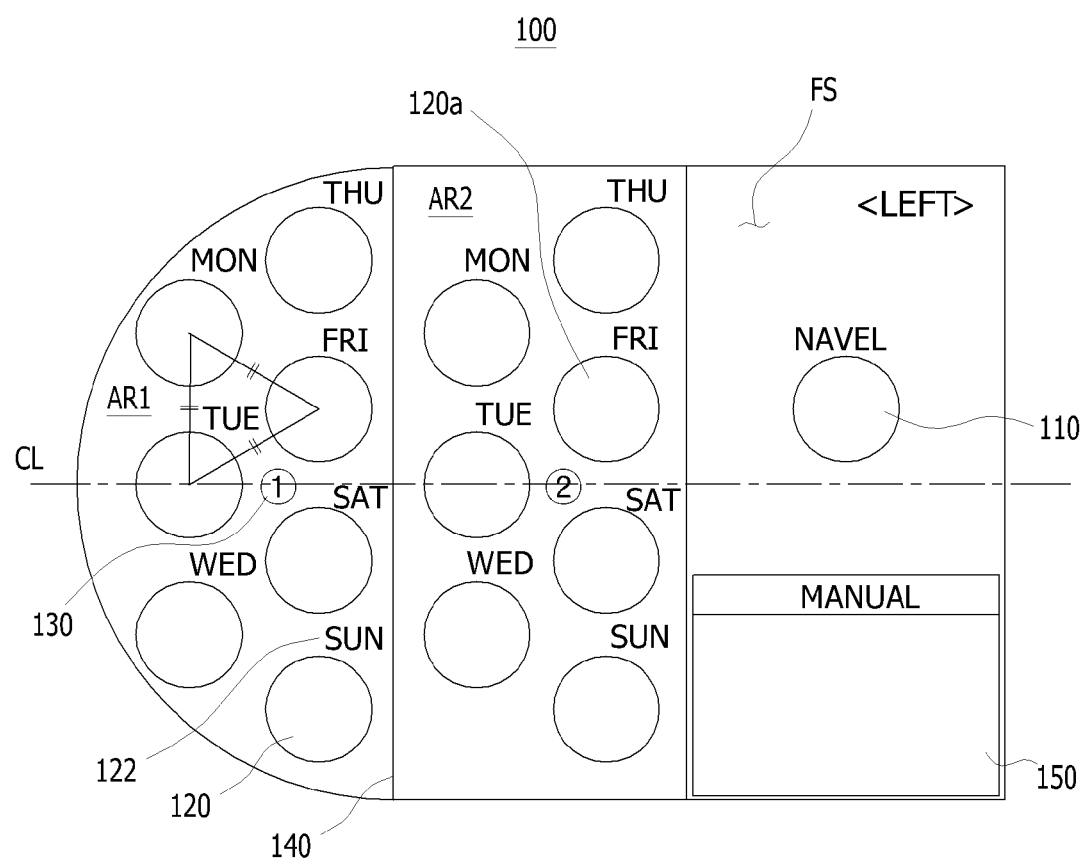

[FIG. 2]
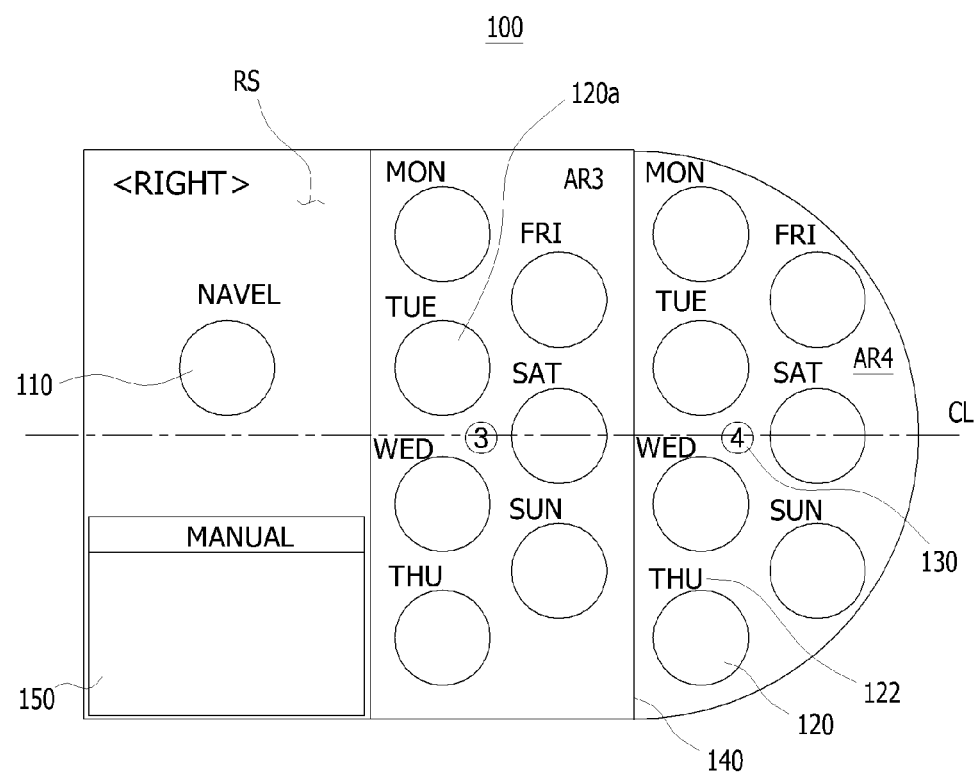

[FIG. 3]
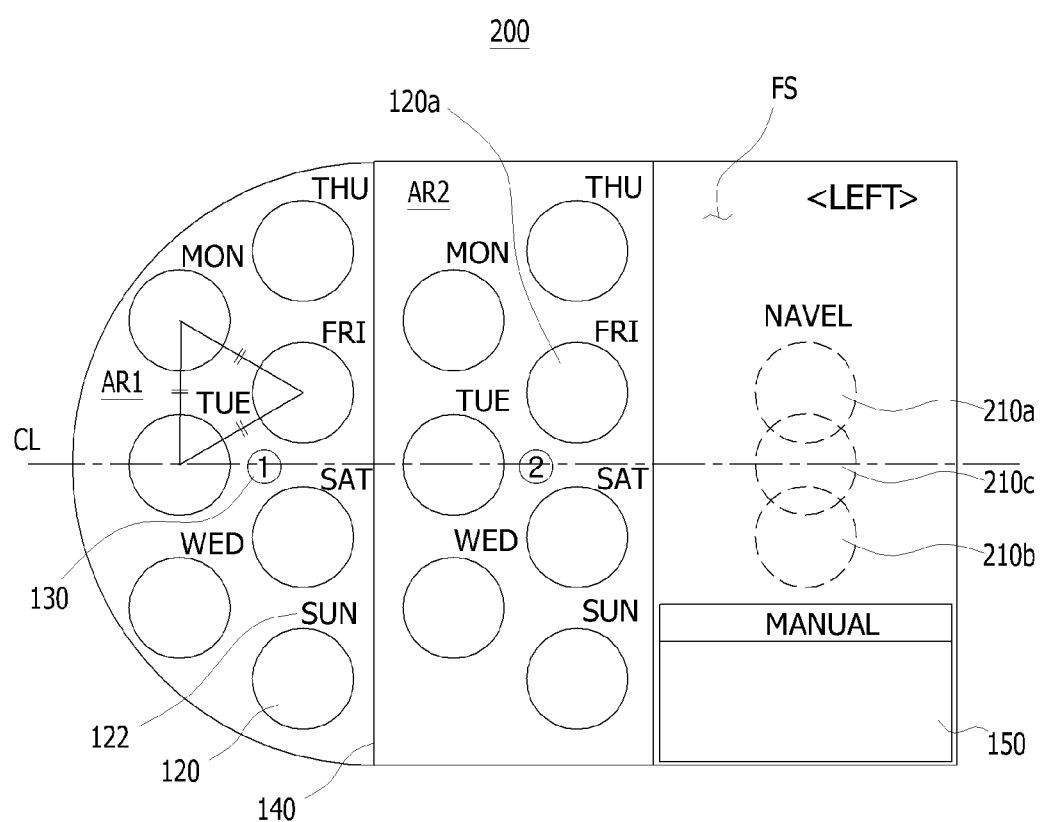

SHEET FOR GUIDING LOCATION OF INSULIN INJECTION

CROSS REFERENCE TO RELATED APPLICATION

This application claims priority from and the benefit of Korean Patent Application No. 20-2009-0001053, filed on Feb. 2, 2009, which is hereby incorporated by reference for all purposes as if fully set forth herein.

BACKGROUND OF THE INVENTION

1. Field of the Invention

Exemplary embodiments of the present invention relate to a sheet for guiding location of insulin injection. More particularly, a sheet for guiding location of insulin injection capable of easily injecting insulin into a body.

2. Discussion of the Background

Generally, diabetes is a disease that there is too much glucose in blood due to lack or malfunction of insulin secretion so that glucose is found in urine.

It is necessary that diabetes patients should be externally provided with insulin in order to supplement an amount of insulin required in their bodies, and a method of injecting insulin by using an injector has been used. The diabetes patients are required to be repetitively injected once or several times a day, and the injection spot is generally selected as a subcutaneous fat in which few nervous system exists and from which a joint is distant.

When insulin is repetitively injected at the same spot of a patient, lipohyperplasia may occur to the patient. Thus, the patient is required to continuously move an injection spot. However, there exists a problem that it is difficult for the patient to properly move the injection spot, when the patient injects insulin once or several times a day for himself or herself.

In order to solve the above problems, a sheet for guiding location of insulin injection has been used. A conventional sheet covers patient's abdomen, and a reference hole is formed through the conventional sheet corresponding to patient's navel. In the conventional sheet, injection holes are symmetrically formed at both sides from the reference hole, and the injection holes are numbered one by one from number 1 to guide an injection location.

However, the conventional sheet enforces the patient to memorize a number previously used, and the conventional sheet can be used only in abdomen so that the conventional sheet is hard to be used at other location except for the abdomen. In addition, since a circulation criterion is uniformly applied compared with various injection methods, a patient may be confused for an injection location and an injection dose, and a distance between the navel located at a center and the outermost injection holes located at both sides is great so that it may happen that the outermost injection holes exceed the patient's abdomen.

Accordingly, a sheet for guiding location of insulin injection is required to be improved for user's convenience.

SUMMARY OF THE INVENTION

Exemplary embodiments of the present invention provide a sheet for guiding location of insulin injection capable of enhancing user's convenience.

An exemplary embodiment of the present invention discloses a sheet for guiding location of insulin injection having a sheet shape. The sheet has a first face and a second face opposite to the first face. A reference mark is formed at a first portion of the sheet to correspond to user's navel. A plurality of injection holes is formed at a second portion of the sheet opposite to the first portion to inject insulin, so that the insulin is injected at a left portion with respect to the reference mark by using the first face and the insulin is injected at a right portion with respect to the reference mark. A manual of the sheet is indicated on the first face and/or the second face. A day of a week is indicated corresponding to and adjacent to each of the injection holes.

In an exemplary embodiment, the manual may be indicated adjacent to the reference mark, and may be attached to the first face and/or the second face in a sticker form.

In an exemplary embodiment, the sheet may have a first area, a second area, a third area and a fourth area. The first area is located distant from the reference mark when viewed from the first face, and at least seven injection holes are formed through the first area. The second area is located near to the reference mark when viewed from the first face, and at least seven injection holes are formed through the second area. The third area is located near to the reference mark when viewed from the second face, and at least seven injection holes are formed through the third area. The fourth area is located distant from the reference mark when viewed from the second face, and at least seven injection holes are formed through the fourth area. An area number may be indicated on each of the first, second, third and fourth areas.

In an exemplary embodiment, the first and second areas may be divided by a section line or different colors, and the third and fourth areas may be divided by a section line or different colors.

In an exemplary embodiment, three injection holes may be formed distant from the reference mark to define a first column and four injection holes are formed near to the reference mark to define a second column, in each of the first and fourth areas, and the sheet may be rounded in a direction from the second column to the first column.

For example, the injection holes corresponding to the first column and the injection holes corresponding to the second column may be alternately arranged from each other.

For example, a distance between the reference mark and the nearest injection hole to the reference mark may range from about 3 cm to about 5 cm, and an interval between centers of adjacent injection holes may be less than about 3 cm.

In an exemplary embodiment, an upper portion and a lower portion of the sheet is defined based on a direction in which letters disclosed on the sheet are uprightly viewed, and the reference mark may be formed at the upper portion. Alternatively, the reference mark may be formed at the upper portion, at the lower portion and at a portion between the upper portion and the lower portion.

According to the above, a sheet is formed so that insulin may be injected on a left portion of the patient's abdomen by using a front face of the sheet and insulin may be injected on a right portion of the patient's abdomen by using a rear face of the sheet. Thus, the length from left to right of the sheet is greatly reduced, such that convenience of portability for the patient who is required to inject insulin at anytime and anywhere may be improved, and the patient also easily injects insulin into his or her body by using the sheet having a reduced size when the patient injects insulin on his or her arms and legs in addition to the abdomen.

Also, the patient may easily know and memorize an order of injecting insulin with reference to an area number indicating each area and an injection day of the week indicating a day when to inject insulin into his or her body, and may easily inject insulin at a location spaced apart from a previously injected location by a predetermined distance with a selected rule whenever the patient injects the insulin.

In addition, since the injection areas may be divided by a section line or different colors, even a patient having poor eyes may easily discriminate the areas. The number of the injection holes formed at a location distant from the reference mark may be greater than the number of the injection holes formed at a location near to the reference mark, thereby guiding injection spots to be located at the abdomen.

Further, a distance from the reference mark corresponding to the navel to the injection holes may be reduced, and the injection holes may be uniformly arranged, thereby effectively using the patient's limited abdomen area.

Also, the manual may be disclosed on the sheet to guide a method of injecting insulin using the sheet, which may be confused to the patient, thereby preventing the patient from being confused for using the sheet.

In addition, the reference mark of the sheet may be formed at the upper portion of the central line. Thus, when a patient locates the sheet on his or her abdomen with reference to the navel, letters disclosed on the sheet are uprightly viewed by the patient, thereby enhancing the patient's convenience. Alternatively, a plurality of reference marks may be formed at various locations, and the reference marks may be provided according to a body type of each patient, thereby enhancing the patient's convenience.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIG. 1 is a front view illustrating a sheet for guiding location of insulin injection according to an exemplary embodiment of the present invention.

FIG. 2 is a rear view illustrating the sheet for guiding location of insulin injection illustrated in FIG. 1.

FIG. 3 is a front view illustrating a sheet for guiding location of insulin injection according to another exemplary embodiment of the present invention.

DETAILED DESCRIPTION OF THE ILLUSTRATED EMBODIMENTS

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be described in detail with reference to the accompanying drawings.

FIG. 1 is a front view illustrating a sheet for guiding location of insulin injection according to an exemplary embodiment of the present invention. FIG. 2 is a rear view illustrating the sheet for guiding location of insulin injection illustrated in FIG. 1.

Referring to FIGS. 1 and 2, a sheet 100 for guiding location of insulin injection according to an exemplary embodiment of the present invention has a first face FS corresponding to a front face and a second face RS corresponding to a rear face opposite to the first face FS, and has a sheet shape.

A reference mark 110 and a plurality of injection holes 120 are formed at the sheet 100.

The reference mark 110 is formed at a first portion of the sheet 100, for example, a right portion of the first face FS or a left portion of the second face RS as shown in FIGS. 1 and 2 to correspond to user's navel. For example, the reference mark 110 may be formed in a hole form to pass through the sheet 100.

The injection holes 120 are formed at a second portion of the sheet 100 opposite to the first portion of the sheet 100, for example, a left portion of the first face FS as shown in FIG. 1. The injection holes 120 are formed at only one portion with respect to the reference mark 110. Particularly, the injection holes 120 are formed at the second portion of the sheet 100, so that the insulin is injected at a left portion with respect to the reference mark 110 on the first face FS and the insulin is injected at a right portion with respect to the reference mark 110 on the second face RS.

As described above, the sheet 100 for guiding location of insulin injection according to an exemplary embodiment of the present invention is not formed to longitudinally extend so that insulin is injected on both a left portion and a right portion of patient's abdomen on only one face, as is employed in a conventional sheet, and the sheet 100 is formed so that the insulin may be injected on a left portion of the patient's abdomen by using the front face of the sheet 100 and the insulin may be injected on a right portion of the patient's abdomen by using the rear face of the sheet 100. Thus, the length from left to right of the sheet 100 is greatly reduced, such that convenience of portability for the patient who is required to inject insulin at anytime and anywhere may be improved, and the patient also easily injects insulin into his or her body by using the sheet 100 having a reduced size when the patient injects insulin on his or her arms and legs in addition to the abdomen.

In an exemplary embodiment, the sheet 100 may have a first area AR1, a second area AR2, a third area AR3 and a fourth area AR4. An area number 130 may be indicated on each of the first, second, third and fourth areas AR1, AR2, AR3 and AR4.

The first area AR1 may be located distant from the reference mark 110 when viewed from the first face FS, for example, located at a left portion of the first face FS as shown in FIG. 1. The second area AR2 may be located near to the reference mark 110 when viewed from the first face FS, for example, located at a central portion of the first face FS as shown in FIG. 1. The third area AR3 may be located near to the reference mark 110 when viewed from the second face RS, for example, located at a central portion of the second face RS as shown in FIG. 2. The fourth area AR4 may be located distant from the reference mark 110 when viewed from the second face RS, for example, located at a right portion of the second face RS as shown in FIG. 2.

At least seven injection holes 120 may be formed in each of the first, second, third and fourth areas AR1, AR2, AR3 and AR4, and an injection day 122 of the week may be indicated corresponding to and adjacent to each of the injection holes 120. Thus, the user may know an order of injecting the insulin with reference to the area number 130 indicating each area and the injection day 122 of the week indicating a day when to inject insulin into his or her body.

For example, in case of a patient who injects insulin into his or her body once a day, the patient may check '①' of the area number 130 indicating the first area AR1, and then inject insulin with reference to the injection day 122 corresponding to that day of the week. Thereafter, next week, the patient may check '②' of the area number 130 indicating the second area AR2, and then inject insulin with reference to the injection day 122 corresponding to that day of the week. Thereafter, next week, the patient may check '③' of the area number 130, and then inject insulin with reference to the injection day 122 of the week. Thereafter, next week, the patient may check '④' of the area number 130, and then inject insulin with reference to the injection day 122 of the week.

For another example, in case of a patient who injects insulin into his or her body twice a day, in the morning, the patient may check '①' of the area number 130 indicating the first area AR1, and then inject insulin with reference to the injection day 122 corresponding to that day of the week. Thereafter, in the afternoon, the patient may check '②' of the area number 130 indicating the second area AR2, and then inject insulin with reference to the injection day 122 corresponding to that day of the week. Thereafter, next week, the patient may check '③' of the area number 130, and then inject insulin with reference to the injection day 122 of the week in the morning. Thereafter, the patient may check '④' of the area number 130, and then inject insulin with reference to the injection day 122 of the week in the afternoon.

For still another example, in case of a patient who injects insulin into his or her body three times a day, in the morning, the patient may check '①' of the area number 130 indicating the first area AR1, and then inject insulin with reference to the injection day 122 corresponding to that day of the week. Thereafter, in the afternoon, the patient may check '②' of the area number 130 indicating the second area AR2, and then inject insulin with reference to the injection day 122 corresponding to that day of the week. Thereafter, in the evening, the patient may check '③' of the area number 130, and then inject insulin with reference to the injection day 122 of the week.

For still another example, in case of a patient who injects insulin into his or her body four times a day, in the daybreak, the patient may check '①' of the area number 130 indicating the first area AR1, and then inject insulin with reference to the injection day 122 corresponding to that day of the week. Thereafter, in the morning, the patient may check '②' of the area number 130 indicating the second area AR2, and then inject insulin with reference to the injection day 122 corresponding to that day of the week. Thereafter, in the afternoon, the patient may check '③' of the area number 130, and then inject insulin with reference to the injection day 122 of the week. Thereafter, in the evening, the patient may check '④' of the area number 130, and then inject insulin with reference to the injection day 122 of the week.

Thus, a patient may know and memorize an order of injecting the insulin with reference to the area number 130 indicating each area and the injection day 122 of the week indicating a day when to inject insulin into his or her body, and may easily inject insulin at a location spaced apart from a previously injected location by a predetermined distance with a selected rule whenever the patient injects the insulin.

An order of the areas may be set different from the above examples. For example, the area numbers '①' and '③' may be located on the first face FS corresponding to a front face, and the area numbers '②' and '④' may be located on the second face RS corresponding to a rear face. Thus, the sheet 100 may be manufactured so that the order of the areas is different from the order shown in FIGS. 1 and 2.

The first and second areas AR1 and AR2 may be divided by a section line 140 or different colors, and the third and fourth areas AR3 and AR4 may be also divided by a section line 140 or different colors. Thus, even a patient having poor eyes may easily discriminate the areas.

In each of the first, second, third and fourth areas AR1, AR2, AR3 and AR4, three injection holes 120 are formed distant from the reference mark 110 to define a first column and four injection holes 120 are formed near to the reference mark 110 to define a second column. Thus, seven injection holes 120 may be properly distributed and disposed according to each day of the week, and the injection holes 120 are formed so that the injection holes 120 in the first area AR1 and the fourth area AR4 that are located near to user's flank are not located adjacent to rib or groin, thereby guiding injection spots to be located at the abdomen.

In addition, as shown in FIGS. 1 and 2, the sheet 100 may be rounded in a direction from the second column to the first column. Thus, a patient may have stability of the injection spots and manufacturing cost may be reduced due to reduced material.

The injection holes 120 corresponding to the first column and the injection holes 120 corresponding to the second column may be alternately arranged from each other. For example, as shown in FIGS. 1 and 2, adjacent injection holes 120 of the injection holes 120 corresponding to the first and second column may be formed to have almost the same distance between centers thereof, thereby forming an equilateral triangle. Accordingly, the injection holes 120 may be uniformly arranged, and thus patient's limited abdomen area may be effectively used in comparison with conventional injection holes that are arranged in parallel with each other.

A distance between the reference mark 110 and the nearest injection hole 120a to the reference mark 110 may range from about 3 cm to about 5 cm. Thus, a horizontal length may be reduced based on a navel in comparison with a conventional horizontal length, to thereby improve a problem that in case of a tiny patient, insulin may be injected into a portion near to his or her flank. In addition, an interval between the centers of the adjacent injection holes 120 may be less than about 3 cm. That is, with regard to the injection holes 120 corresponding to the first column or the second column, since not only an interval between centers of adjacent injection holes 120 corresponding to the same column but an interval between centers of adjacent injection holes 120 corresponding to the different columns is also within a predetermined distance, patient's limited abdomen area may be effectively used in comparison with conventional injection holes that are arranged in parallel with each other as described above.

Since there exist various insulin injection methods as described above, a patient may be confused. Thus, a manual 150 of the sheet 100 may be indicated on the first face FS and/or the second face RS. For example, as shown in FIGS. 1 and 2, the manual 150 of the sheet 100 may be indicated on a lower portion of the reference mark 110. The manual 150 may include, for example, injection order, injection time, injection dose, etc. of the injection hole 120, and may be directly written on the sheet 100 or attached to the sheet 100 in a sticker form after patients are instructed in the above instructions. Thus, patients may be prevented from confusion in real use, in comparison with a conventional sheet on which a manual is not disclosed so that patients use the conventional sheet just dependent on oral instructions.

When an upper portion and a lower portion of the sheet are defined based on a direction in which letters disclosed on the sheet are uprightly viewed, the reference mark 110 may be formed at the upper portion, i.e., an upper portion of a central line CL. Since it is generally inconvenient for patients to partially take off their pants in case that insulin is injected into too lower portion of the body, the injection holes of the sheet for guiding location of insulin injection is generally formed to be located at an upper portion with respect to the patient's navel for patient's convenience. However, in a conventional sheet, a reference hole corresponding to the navel is formed at a central portion or a lower portion of the conventional sheet. Thus, when a patient locates the sheet on his or her abdomen with reference to the navel, there exists letters disclosed on the sheet are viewed upside down by the patient, thereby incurring the patient's inconvenience. In case that the reference mark 110 of the sheet 100 is formed at the upper portion according to an exemplary embodiment of the present invention as described above, when a patient locates the sheet 100 on his or her abdomen with reference to the navel, letters such as the area number 130, an injection day of the week 122, manual 150, etc. is uprightly viewed by the patient, thereby enhancing patient's convenience.

For the above reasons, the injection holes of the sheet is generally formed to be located at an upper portion with respect to the patient's navel for patient's convenience, but it may be undesirable according to a body type of each patient that the injection holes are located at the upper portion with respect to the patient's navel. Thus, a plurality of reference marks 110 may be formed. Hereinafter, an exemplary embodiment for the plurality of reference marks 110 will be described in detail with reference to the accompanying drawing.

FIG. 3 is a front view illustrating a sheet for guiding location of insulin injection according to another exemplary embodiment of the present invention. A sheet 200 for guiding location of insulin injection shown in FIG. 3 is substantially the same as the sheet 100 in FIGS. 1 and 2 except for a plurality of reference marks 210a, 210b and 210c. Thus, any further description will be omitted.

Referring to FIG. 3, a sheet 200 for guiding location of insulin injection according to another exemplary embodiment of the present invention includes a first reference mark 210a, a second reference mark 210b and a third reference mark 210c. For example, the first, second and third reference marks 210a, 210b and 210c may be indicated only in a dotted line form, which is different from the reference mark 110 shown in FIGS. 1 and 2. Alternatively, the number of the reference marks is not limited to three, and may be two, four or more, and the reference marks may be indicated in various forms such as a continuous line.

Thus, a location of the reference mark may be selected according to a body type of each patient, for example, when instructing insulin injection patient. For example, it may be guided that one of the first, second and third reference marks 210a, 210b and 210c indicated in a dotted line form is selected, or the instructor may directly form a hole and distribute the hole-formed sheet to a patient.

According to the sheet 100 of the present invention, the sheet 100 is formed so that the insulin may be injected on a left portion of the patient's abdomen by using the front face of the sheet 100 and the insulin may be injected on a right portion of the patient's abdomen by using the rear face of the sheet 100. Thus, the length from left to right of the sheet 100 is greatly reduced, such that convenience of portability for the patient who is required to inject insulin at anytime and anywhere may be improved, and the patient also easily injects insulin into his or her body by using the sheet 100 having a reduced size when the patient injects insulin on his or her arms and legs in addition to the abdomen.

Also, the patient may easily know and memorize an order of injecting the insulin with reference to the area number 130 indicating each area and the injection day 122 of the week indicating a day when to inject insulin into his or her body, and may easily inject insulin at a location spaced apart from a previously injected location by a predetermined distance with a selected rule whenever the patient injects the insulin.

In addition, since the injection areas AR1, AR2, AR3 and AR4 may be divided by a section line 140 or different colors, even a patient having poor eyes may easily discriminate the areas. The number of the injection holes 120 formed at a location distant from the reference mark 110 may be greater than the number of the injection holes 120 formed at a location near to the reference mark 110, thereby guiding injection spots to be located at the abdomen.

Further, a distance from the reference mark 110 corresponding to the navel to the injection holes 120 may be reduced, and the injection holes 120 may be uniformly arranged, thereby effectively using the patient's limited abdomen area.

Also, the manual 150 may be disclosed on the sheet 100 to guide a method of injecting insulin using the sheet 100, which may be confused to the patient, thereby preventing the patient from being confused for using the sheet 100.

In addition, the reference mark 110 of the sheet 100 may be formed at the upper portion of the central line CL. Thus, when a patient locates the sheet on his or her abdomen with reference to the navel, letters disclosed on the sheet 100 are uprightly viewed by the patient, thereby enhancing the patient's convenience. Alternatively, a plurality of reference marks may be formed at various locations, and the reference marks 210a, 210b and 210c may be provided according to a body type of each patient, thereby enhancing the patient's convenience.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A sheet for guiding location of insulin injection having a sheet shape, the sheet comprising:
   a first face and a second face opposite to the first face,
   a reference mark formed on the sheet to correspond to a user's navel,
   a plurality of injection holes formed through the sheet to inject insulin, the injection holes being formed at only one portion of a left portion and a right portion with respect to the reference mark, so that the insulin is injected through the injection holes formed at the left portion with respect to the reference mark by using the first face when the insulin is injected at a left portion with respect to the user's navel and the insulin is injected through the injection holes formed at the right portion with respect to the reference mark by using the second face when the insulin is injected at a right portion with respect to the user's navel,
   a manual of the sheet indicated on at least one of the first face and the second face,
   a day of a week indicated corresponding to and adjacent to each of the injection holes,
   wherein the sheet has:
      a first area located distant from the reference mark when viewed from the first face, at least seven injection holes being formed through the first area;
      a second area located near to the reference mark when viewed from the first face, at least seven injection holes being formed through the second area;
      a third area located near to the reference mark when viewed from the second face, at least seven injection holes being formed through the third area; and
      a fourth area located distant from the reference mark when viewed from the second face, at least seven injection holes being formed through the fourth area,
   wherein the first area and the fourth area form both sides of a same part of the sheet, and the at least seven injection holes of the first area and the at least seven injection holes of the fourth area are same,
   wherein the second area and the third area form both sides of a same part of the sheet, and the at least seven injection holes of the second area and the at least seven injection holes of the third area are same, and
   wherein an area number is indicated on each of the first, second, third and fourth areas.

2. The sheet of claim 1, wherein the manual is indicated adjacent to the reference mark, and is attached to the first face and/or the second face in a sticker form.

3. The sheet of claim 1, wherein the first and second areas are divided by a section line or different colors, and the third and fourth areas are divided by a section line or different colors.

4. The sheet of claim 1, wherein three injection holes are formed distant from the reference mark to define a first column and four injection holes are formed near to the reference mark to define a second column, in each of the first and fourth areas, and the sheet is rounded in a direction from the second column to the first column.

5. The sheet of claim 4, wherein the injection holes corresponding to the first column and the injection holes corresponding to the second column are alternately arranged from each other.

6. The sheet of claim 1, wherein a distance between the reference mark and the nearest injection hole to the reference mark ranges from about 3 cm to about 5 cm, and an interval between centers of adjacent injection holes is less than about 3 cm.

7. The sheet of claim 1, wherein an upper portion and a lower portion of the sheet are defined based on a direction in which letters disclosed on the sheet are uprightly viewed, and the reference mark is formed at the upper portion.

8. The sheet of claim 1, wherein an upper portion and a lower portion of the sheet are defined based on a direction in which letters disclosed on the sheet are uprightly viewed, and the reference mark is formed at the upper portion, at the lower portion and at a portion between the upper portion and the lower portion.

* * * * *